(12) United States Patent
Mauge et al.

(10) Patent No.: US 8,231,563 B2
(45) Date of Patent: Jul. 31, 2012

(54) ELECTROKINETIC ACTUATOR TO TITRATE FLUID FLOW

(75) Inventors: Christophe P. Mauge, Doylestown, PA (US); Ramakrishna Venugopalan, Holliston, MA (US)

(73) Assignee: Codman Neuro Sciences Sarl, LeLocle (CH)

( * ) Notice: Subject to any disclaimer, the term of this patent is extended or adjusted under 35 U.S.C. 154(b) by 273 days.

(21) Appl. No.: 12/655,404

(22) Filed: Dec. 30, 2009

(65) Prior Publication Data

US 2011/0160638 A1    Jun. 30, 2011

(51) Int. Cl.
*A61M 5/00* (2006.01)
*C02F 1/40* (2006.01)
(52) U.S. Cl. .................. 604/9; 604/8; 204/600
(58) Field of Classification Search .......... 604/8, 9; 204/600
See application file for complete search history.

(56) References Cited

U.S. PATENT DOCUMENTS

| | | | |
|---|---|---|---|
| 4,595,390 A * | 6/1986 | Hakim et al. ............. | 604/9 |
| 6,013,164 A | 1/2000 | Paul et al. | |
| 6,019,882 A | 2/2000 | Paul et al. | |
| 6,406,605 B1 * | 6/2002 | Moles .................. | 204/601 |
| 7,217,351 B2 * | 5/2007 | Krumme ............... | 204/600 |
| 7,297,246 B2 | 11/2007 | Patel | |
| 7,367,968 B2 | 5/2008 | Rosenberg et al. | |
| 2002/0026139 A1 | 2/2002 | Bertrand et al. | |
| 2005/0045480 A1 | 3/2005 | Krumme | |
| 2005/0055009 A1 | 3/2005 | Rosenberg | |
| 2008/0154215 A1 | 6/2008 | Rosenberg et al. | |

FOREIGN PATENT DOCUMENTS

| | | |
|---|---|---|
| EP | 1 380 317 | 1/2004 |
| EP | 1 491 232 | 12/2004 |
| EP | 1 642 613 | 4/2006 |

OTHER PUBLICATIONS

Website "www.neurosurgery.pitt.edu/endovascular/treatments/nph.html" (Jun. 24, 2009)(3 pages).
European Search Report dated Apr. 18, 2012 for counterpart EP Application No. 10252240.6 (6 pages).

* cited by examiner

*Primary Examiner* — Leslie Deak
(74) *Attorney, Agent, or Firm* — Cheryl F. Cohen, LLC

(57) ABSTRACT

An electrokinetic actuator for fluid flow titration including two chambers separated from one another by a porous dielectric disposed therebetween. A plurality of electrodes are disposed about a perimeter of the first and second chambers. Polar electrolyte disposed within the actuator is able to pass through the porous dielectric between the first and second chambers upon the application of an electric field or electric potential to the plural electrodes. A mechanical valve actuation mechanism connected to the second chamber allows for fine titration of fluid flow using electro-osmosis, including full-flow and/or complete cut-off. The polar electrolyte is isolated to prohibit intermixing with a fluid being titrated (such as cerebrospinal fluid).

15 Claims, 7 Drawing Sheets

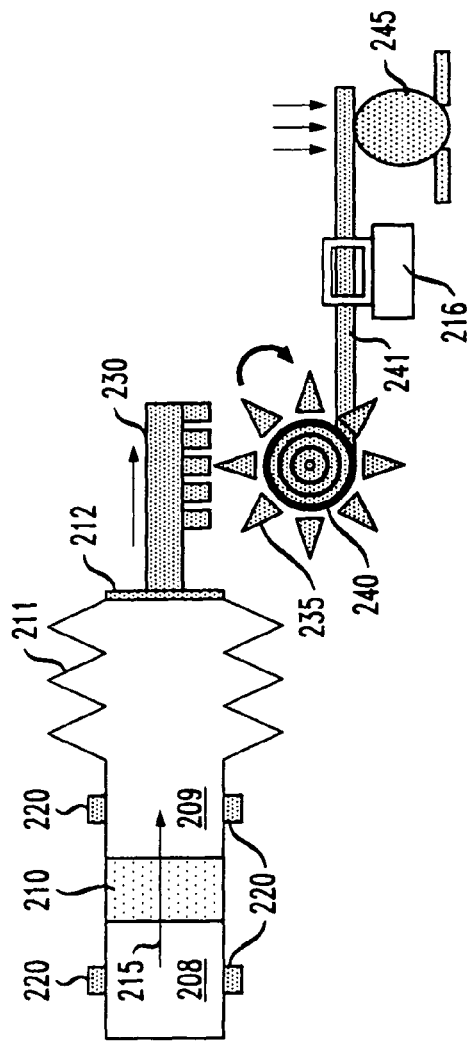
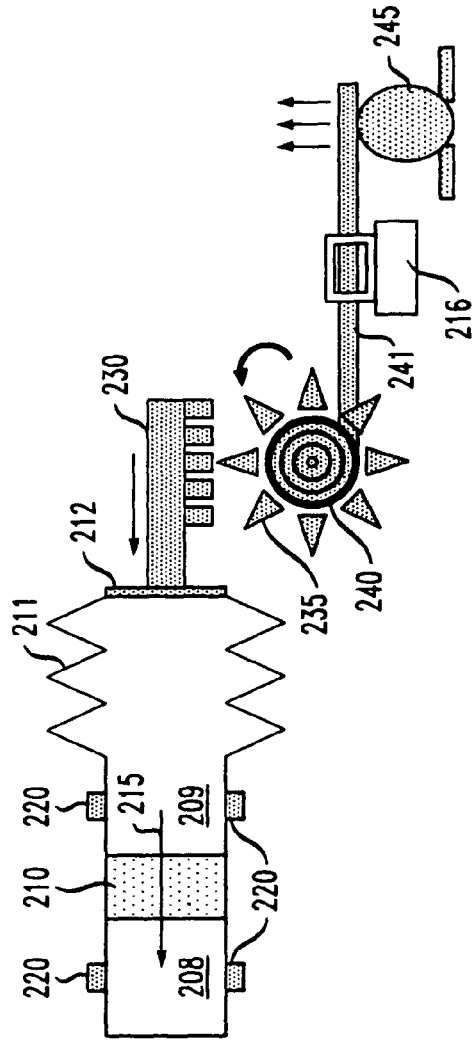
FIG. 3A
FIG. 3B

ELECTROKINETIC ACTUATOR TO TITRATE FLUID FLOW

BACKGROUND OF THE INVENTION

1. Field of the Invention

The present invention relates to a method and apparatus for managing hydrocephalus in a patient. More particularly, the invention relates to a method and apparatus for adjusting, controlling or programming the drainage rate of cerebrospinal fluid (CSF) in a hydrocephalus patient. Even more particularly, the invention relates to a shunt system for varying the opening pressure and/or diameter of the shunt and thus controlling the rate of fluid flow (drainage) of cerebrospinal fluid from a ventricular cavity.

2. Description of Related Art

Hydrocephalus is a condition afflicting patients who are unable to regulate cerebrospinal fluid flow through their body's own natural pathways. Cerebrospinal fluid (CSF) is normally produced by the choroid plexus of the brain and carries essential nutrients, hormones, and other cellular components to various portions of the brain as the fluid circulates through the ventricular system. Moreover, the CSF also helps absorb shock and cushions the brain as the fluid diffuses over the brain and spinal cord. Cerebrospinal fluid that is not recirculated eventually drains into the sagittal sinus where it is naturally absorbed by the body's venous system. In a patient suffering from hydrocephalus, the CSF absorption rate fails to keep up with the production rate, either because of an obstruction along the natural CSF pathway or due to diseased choroid plexus which increases CSF formation. The unabsorbed or excess CSF accumulates in the ventricles of the patient's brain, leading to an increase in intracranial pressure. If left untreated, the increased intracranial pressure can lead to serious medical conditions such as compression of the brain tissue and impaired blood flow to the brain, with such potential consequences as coma and/or death.

The conventional treatment for hydrocephalus patients has involved draining the excess fluid away from the ventricles and rerouting the excess CSF to another area of the patient's body, such as the peritoneum (abdomen) or vascular system. An implantable drainage system, commonly referred to as a shunt such as that disclosed in U.S. Pat. No. 4,595,390, is often used to transfer fluid so as to restore the balance between the production and absorption of CSF in the patient.

The shunt has several basic components. A first portion is the called the proximal, head or ventricular catheter implanted into the ventricular cavity of the patient's brain. The proximal catheter, in turn, is connected to the valve and reservoir. The valve controls how much fluid is drained from the brain, it is then stored in the reservoir until it is released to pass via the distal, peritoneum or drainage catheter. Once again, the distal or drainage catheter leads the excess CSF to drain to a predetermined absorption site (e.g., the abdomen (peritoneum)) of the patient's body where it will be absorbed.

A shunt performs two basic operations or functions. It allows the fluid to flow only in one direction when the intracranial pressure has exceeded some predetermined value (usually referred to as the "opening pressure" for the shunt). This system regulates the amount of the CSF in the body so that the correct amount of fluid (neither too much, nor too little) is released from the brain.

To regulate the flow of cerebrospinal fluid between the proximal and distal ends of the shunt system, the main body of the shunt usually includes a pump or a control valve. Generally, shunt systems include a valve mechanism that operates by permitting fluid flow only once the fluid pressure reaches a certain threshold level. That is, fluid enters the valve only when the fluid pressure overcomes the valve mechanism's resistance to open. Some valve mechanisms permit the non-invasive adjustment, or programming, of the opening pressure level at which fluid flow commences.

Shunts having valve mechanisms that continuously drain CSF at a fixed rate are well known, as are shunts with valves that control and/or adjust the opening pressure and/or drainage rate of the patient's CSF.

US Patent Publication No. 2005/0055009, assigned to Codman & Shurtleff, Inc., discloses an adjustable drainage system for regulating cerebrospinal fluid flow in a hydrocephalus patient where the drainage rate is adjusted in response to the ventricular volume variations in the patient. The adjustable resistance valve 40 includes a multi lumen catheter 48 having a plurality of different resistances and a selection mechanism 44 by way of a rotatable disc 46 with a single aperture 46a. During adjustment, disc 46 is rotated via an actuator 42 so that the aperture 46 aligns with the lumen having the desired resistance. Selection of the desired resistance for the adjustable resistance valve 40 is achieved by rotation of the actuator 42. This shunt configuration is disadvantageous in that it is limited in the range of resistances offered by the number of different lumens provided. Only step or incremental changes can be made to regulate the drainage as defined by the different resistances employed. Fewer pressure increments produces greater variability. Furthermore, as acknowledged in the publication itself, the resistors are prone to being clogged with particulate matter such as blood cells. Lastly, following implantation, the selection of a particular resistance in the adjustable resistance valve is accomplished using a magnetic tool that influences complementary magnets associated with the implant. As is well known, magnets are subject to unwanted external magnetic influences.

First described by F. F. Reuss in 1809, electro-osmosis is the motion of polar liquid through a membrane or other porous structure under the influence of an applied electric field. U.S. Pat. No. 6,019,882 discloses an electrokinetic high pressure hydraulic system in which an electric potential provides a means for imparting net power to the fluid and by this means to transmit and use this net power to perform work (apply force) on some system. Two specific embodiments are disclosed. A first valve embodiment is shown in FIGS. 1A & 1B. Valve 100 includes a T-shape flow system in which a microchannel 110 contains a porous dielectric 120, extending past outlet 145 about 1-2 channel diameters. Fluid inlet 140 and outlet 145 in communication with microchannel 110 provide for the flow of a fluid (liquid or gas) 150 therethrough. In order to close communication between fluid inlet 140 and outlet 145 an electric potential is applied by a power supply to spaced electrodes 130 to provide the electro-osmotic force required to move electrolyte 115 to close fluid outlet 145, and prevent fluid 150 from flowing through outlet 145. Valve 100 can be opened by simply shutting off the electric potential applied to spaced electrodes 130. In addition, valve 100 can be caused to operate in the opposite direction by simply reversing the sign of the electric potential applied to spaced electrodes 130. In accordance with this embodiment, the electrolyte used in the system (to control flow) mixes with the fluid the system is controlling. Such a mixing of the electrolyte with the CSF is impermissible in an implantable shunt system since the mixed fluid (electrolyte and CSF) would be drained into another location within the body; and introducing such an electrolyte into the body would be detrimental from a biological perspective. Even if such mixing was acceptable, the present inventive system is implanted and thus does not offer ease of access to recharge the pump with new electrolyte to replace the amount that has drained due to operation.

An alternative valve configuration is shown in FIG. 5 of U.S. Pat. No. 6,019,882. In this second embodiment, a cavity is divided into two chambers 20, 25 separated by a fluid tight flexible member 30. A fluid stream enters chamber 25 through fluid inlet line 40 and exits through fluid outlet line 35. The flow of the fluid stream is controlled by applying hydraulic pressure generated by electro-osmotic pump 170 through inlet line 45 to the fluid contained in chamber 20 and, in turn, on flexible member 30 causing it to deform and thereby close off fluid inlet line 40 and stop fluid flow. To open valve 5 the polarity of the electric potential applied to spaced electrodes 130 is reversed. The flow of fluid through fluid inlet line 40 is controllable between one of only two possible states. Valve 5 is either open thereby permitting full flow through the fluid inlet line or closed off completely. This alternative patented embodiment therefore does not permit what is hereinafter referred to as "fine titration" that allows for additional adjustments in fluid flow aside from only the two flow states of full fluid flow (OPEN state) and fluid flow cut off completely (CLOSED state). That is, fine titration is not limited to only two flow states of full fluid flow and fluid flow cut off completely, but is capable of a range of fine adjustments in between.

Neither patented embodiment discloses an electrokinetic pump without intermixing between the pump electrolyte and fluid being finely varied or titrated. Furthermore, the patented system is directed to high-pressure industrial or analytical systems for generating a pressure greater than 2500 psi (corresponding to 172,368.9 mbar or 129,287.3 mmHg) with gross open-close control. In contrast, an implantable programmable shunt system operates at a much lower and limited pressure range with fine titration. Normal intracranial pressure has a baseline in a range of approximately 13 mbar through approximately 20 mbar (corresponding to a range of approximately 10 mmHg through approximately 15 mmHg), with amplitude variations in a range of approximately 4 mbar through approximately 7 mbar (corresponding to a range of approximately 3 mmHg to approximately 5 mmHg). While maximum pathologic values may range from approximately −45 mbar (corresponding to approximately −33 mmHg) to approximately 130 mbar (corresponding to approximately 100 mmHg). Pressures beyond this maximum range may be lethal or at the very least detrimentally affect the patient. Specifically, pressures beyond 500 mbar would be physiologically irrelevant. Use of the present inventive electrokinetic actuator in an implantable shunt valve system would also require the drainage of CSF in relatively small units of ml/day.

It is therefore desirable to develop an electrokinetic actuator capable of adjusting, controlling or programming the fine titration of fluid flow through a valve mechanism, in addition to full fluid flow and/or complete cut off of fluid flow, without any intermixing between the pump electrolyte and fluid being titrated while functioning in the physiological pressure ranges of interest.

SUMMARY OF THE INVENTION

An aspect of the present invention is directed to an electrokinetic actuator for adjusting, controlling or programming fine titration of fluid flow through a valve mechanism without intermixing between the electrolyte and fluid.

Another aspect of the present invention is directed to an electrokinetic actuator for fluid flow titration including a first chamber having a closed proximal end and an opposite open distal end. A second chamber having an open proximal end and an opposite open distal end is separated at its open proximal end from the open distal end of the first chamber by a porous dielectric disposed therebetween. A plurality of electrodes are disposed about a perimeter of the first and second chambers. Polar electrolyte disposed within the actuator is adapted to pass through the porous dielectric between the first and second chambers upon the application of an electric field or electric potential to the plural electrodes. A mechanical valve actuation mechanism connected to the open distal end of the second chamber is used to finely titrate a fluid using electro-osmosis. The polar electrolyte is isolated to prohibit intermixing with the fluid being titrated (such as the CSF).

Still another aspect of the present invention is directed to a method for using the electrokinetic actuator as described in the preceding paragraph.

Yet another aspect of the present invention is directed to the particular use of the previously described electrokinetic actuator in an implantable shunt system for finely titrating cerebrospinal fluid from a proximal catheter to a drainage catheter by controlling an opening pressure and/or diameter of a valve apparatus disposed between the proximal or drainage catheters, wherein fine titration includes full fluid flow and/or complete cut off of fluid flow.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which:

FIGS. 2b and 2c are partial cross-sectional views of the electrokinetic actuator of FIG. 2a, wherein FIG. 2b depicts the electrokinetic actuator at an initial start position and FIG. 2c depicts the electrokinetic actuator at a final position when the actuator pin is displaced due to the application of an electric field;

FIGS. 3a & 3b are schematic diagrams of a combination rotational and translational mechanical valve actuation mechanism for the electrokinetic actuator of FIG. 2a, wherein the mechanical valve actuation mechanism is a rack-n-pinion system in combination with a coil-spring rotating in a clockwise and counter-clockwise direction, respectively;

DETAILED DESCRIPTION OF THE INVENTION

Figure 1:
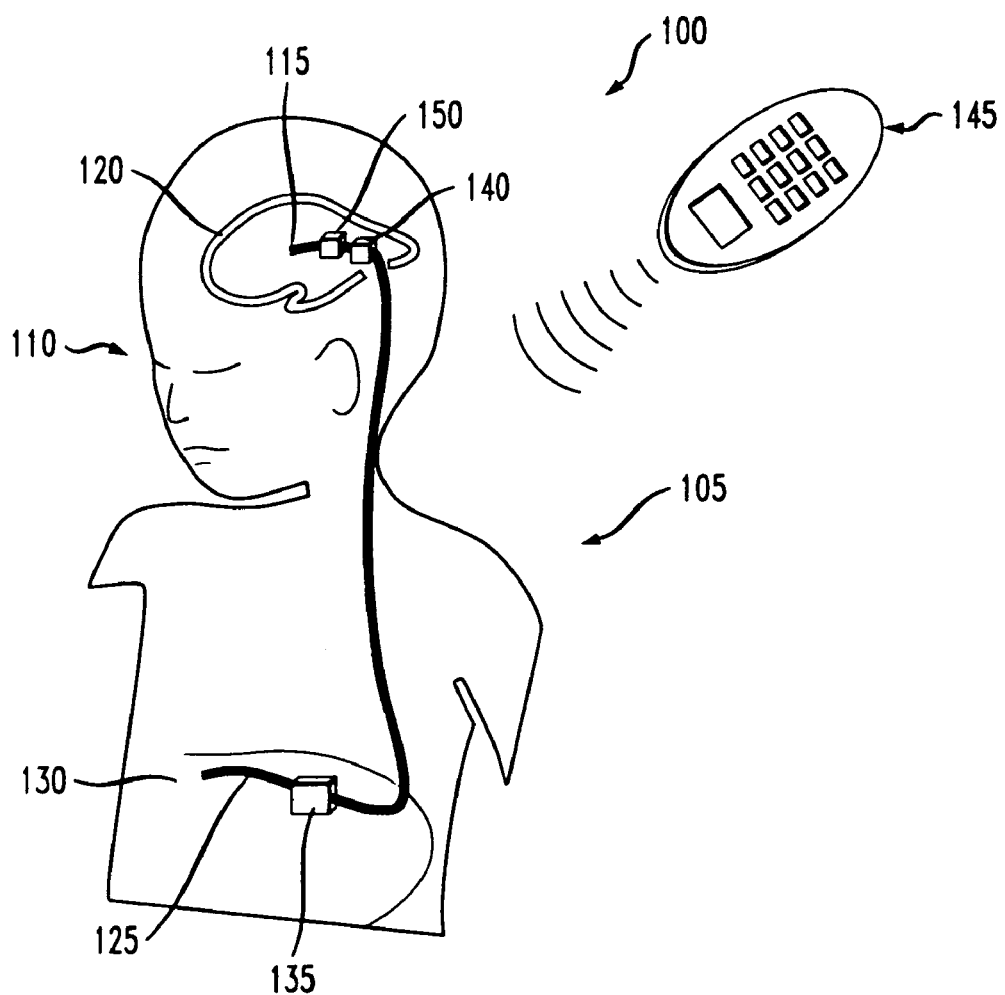
FIG. 1 is a perspective view of an externally programmable implantable shunt system for treatment of a hydrocephalus patient in accordance with the present invention implanted in a patient.

FIG. 1 is an exemplary system 100 including an implantable shunt apparatus 105 implanted within a hydrocephalus patient 110. Shunt apparatus 105 includes a proximal, head or ventricular catheter 115 installed in a ventricular cavity 120 of the patient 110, and a distal, peritoneum or drainage catheter 125 disposed in the peritoneum 130 of the patient 110. Extending between the ventricular and drainage catheters 115, 125 is a programmable valve apparatus 135 for regulating the flow of CSF into and out of the ventricular cavity 120 of the patient 110. The programmable valve apparatus 135 may be disposed anywhere along the fluid pathway of the proximal catheter 115, the distal catheter 125 or therebetween. Preferably, programmable valve apparatus 135 is located within the peritoneal cavity of the patient 110, as illustrated in FIG. 1, so that size constraints for the programmable valve apparatus 135 are minimized (e.g., larger valves can be implanted within the peritoneum than adjacent to the skull).

One or more sensor elements 140 may be used to measure or detect a physiological characteristic of the patient. For example, the single sensor element 140 depicted in FIG. 1 may be a volume sensor for detecting volumetric variations within the ventricular cavity or the ventricular catheter of the patient. Sensor element 140 may be coupled to the programmable valve apparatus 135, or it may be separate therefrom, as shown in FIG. 1. Although shown positioned within the CSF fluid pathway of the shunt system, sensor element 140 may be disposed outside of the CSF fluid pathway while still residing within the ventricular cavity 120 of the patient 110. Furthermore, the sensor element 140 may be eliminated entirely, if desired.

System 100 further includes an external controller 145 to communicate data to and from the implantable shunt apparatus 105 when the external controller is positioned proximate the patient and the shunt apparatus is energized. For example, external controller 145 may be configured to energize and receive an input signal generated from the sensor element 140 that is representative of the measured value of the physiological characteristic. In one particular aspect of the present invention, sensor element 140 is a volume sensor and the physiological characteristic is a measured volume of the ventricular cavity 120 of the patient 110. Sensor element 140 may, measure the volume of fluid flowing through the shunt to monitor proper functioning of the shunt in order to detect a blockage. Alternatively, sensor element 140 may be used to determine the drained volume. This determination of drained volume will disadvantageously consume a significant amount of power. External controller 145 may be configured to generate and transmit to the programmable valve apparatus 135 a control signal that commands the valve to adjust its pressure. The external controller 145 preferably communicates with the implantable shunt wirelessly, e.g., via RF communication.

Implantable shunt apparatus 105 may include more than one sensor element 140 for measuring an additional physiological characteristic of the patient. For example, a second sensor 150 may be a pressure sensor for detecting the ventricular pressure of the patient. Like the first sensor element 140, additional sensor elements transmit data representing a measured or detected value of the additional physiological characteristic to the external controller 145. As with the first sensor, any additional sensors may either be coupled to the valve 135 or be separate therefrom.

Implantable shunt apparatus 105 and external controller 145 of the present invention are equipped with electronic circuitry similar to those for medical telemetry systems that communicate physiological data (e.g., temperature, pressure, etc.) between an implant and a receiver unit. For example, sensor element 140 may be configured to generate an analog signal that is received by the implantable shunt apparatus 105 and converted electronically to a digital pulse. In turn, the digital pulse is transmitted from the implantable shunt apparatus 105 to the external controller 145 wirelessly such as by radiofrequency (RF) communication. Alternatively, any control signal may be processed by the implantable medical device 105 itself using microprocessor 165. One skilled in the art will recognize that these are merely examples of the forms of remote communication suitable for the present invention, and that other forms of non-invasive communication may be utilized without departing from the scope of the present invention.

Figure 2A:
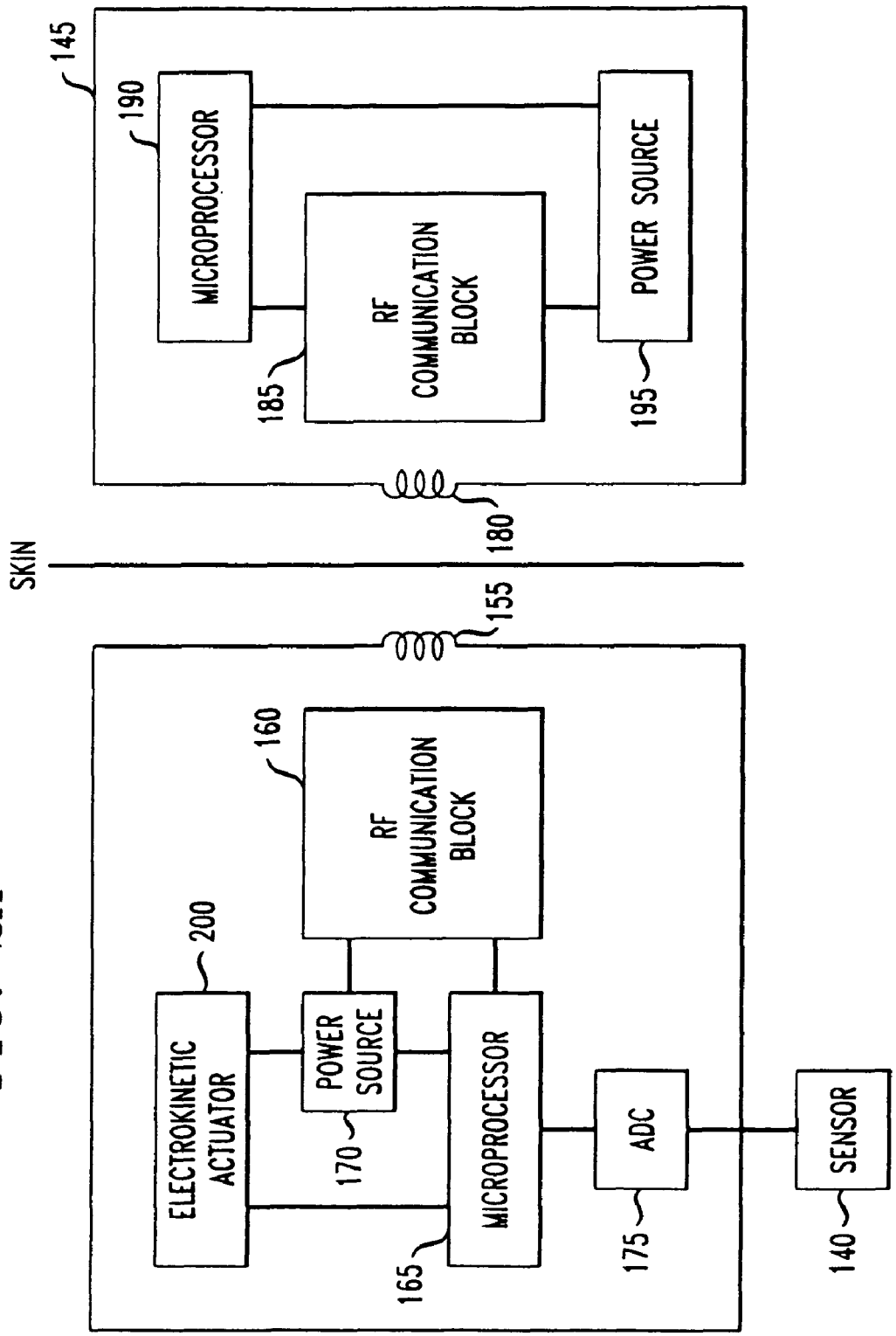
FIG. 2a is a schematic diagram of the implantable shunt apparatus and external controller in the system of FIG. 1 in accordance with the present invention.

An illustrative example of the electronic circuitry in the implantable shunt apparatus 105 and external controller 145 in wireless communication therewith is shown in FIG. 2a. Implantable shunt apparatus 105 has an associated secondary coil 155, RF communication block 160 and microprocessor 165. RF communication block 160 transmits/receives and respectively modulates/demodulates the RF data signals. Internal power source 170 such as a primary battery, smart rechargeable battery or a super capacitor is used to power the implantable medical device 105 and all components and circuitry associated therewith. An analog-to-digital converter (ADC) 175 converts the analog signal generated by the sensor element 140 to a digital signal prior to being processed by the microprocessor 165. Only a single sensor element 140 is shown, however, more than one sensor element may be employed to gather information regarding a physiological characteristic or the sensor element may be eliminated.

External controller 145 includes a primary coil 180 electrically connected to an RF communication block 185 that transmits/receives and respectively modulates the RF data signals. The output of the RF communication block 185 is connected to a microprocessor 190. All components and circuitry associated with the external controller 145 are powered by a power source 195, e.g., a battery or super capacitor. In a preferred embodiment, the power source 195 for powering the external device 145 and its associated circuitry and components is a secondary/rechargeable battery, most preferably a smart rechargeable battery, or a super capacitor. Microprocessor 190 of external controller 145 compares the measured physiological characteristic (e.g., measured volume detected by sensor element 140) to a predetermined target or reference value (e.g., target or reference volume) for the patient 110. The predetermined target value may be ascertained through clinical assessment of the patient 110 and is therefore preferably customized for each particular patient. This target value is then preset or programmed into a memory associated with the external controller 145. During operation, the external controller 145 energizes the implantable shunt apparatus 105 and detects the measured value of the physiological characteristic detected or measured by sensor element 140. Microprocessor 190 associated with external controller 145 determines whether the measured physiological characteristic value is higher than, lower than, or within an acceptable range of the target value. Based on this assessment, the microprocessor 190 then determines whether the opening pressure and/or internal diameter or circumference of the shunt and flow rate of fluid passing therethrough should be increased, decreased or maintained accordingly in order to achieve the target ventricular volume for the patient 110. Once again, such functionality may alternatively be performed in a closed loop manner by the microprocessor 165 of the implantable medical device 105. For instance, the rate of fluid flow or drainage is increased if the measured volume is higher than the target volume; conversely, the flow rate and internal diameter of the shunt is decreased if the measured volume is lower than the target volume. The microprocessor 190 generates an output control signal to control the flow rate of the valve by altering the opening pressure and/or the opening, size, diameter or circumference of the shunt itself. If the measured volume is essentially the same as, or within an acceptable range of the target value, then no adjustment is made.

Figures 2B, 2C:
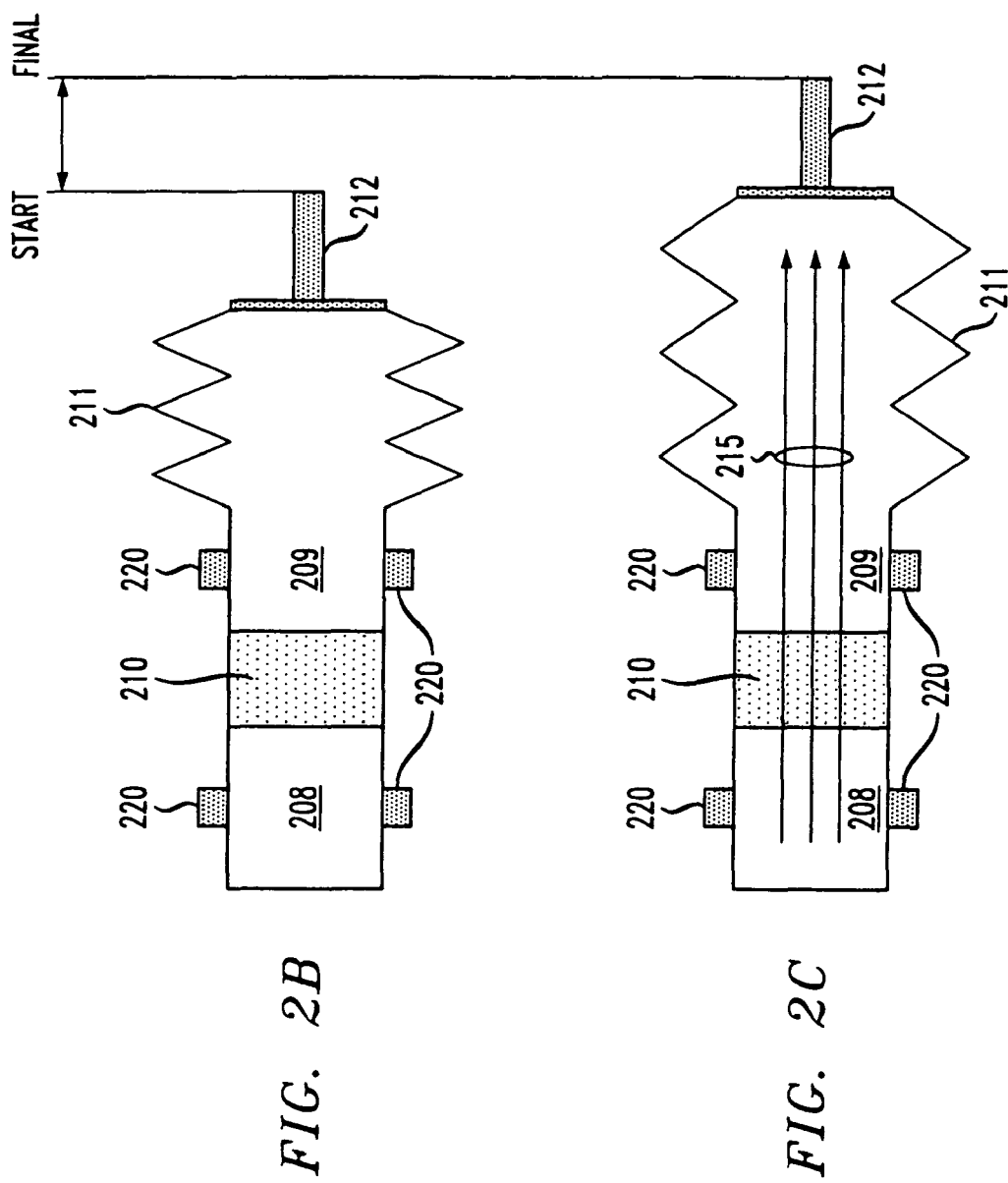

An electrokinetic actuator 200 is used to convert electric potential to a movement or a force that may be used to adjust the valve 135 that controls the drainage rate through the shunt. A basic configuration of the electrokinetic actuator 200 is depicted in FIGS. 2b & 2c. Electrokinetic actuator 200 has two chambers 208, 209 separated by a porous dielectric 210. Chamber 209 is connected to one end of a bellows 211 capable of expanding and collapsing. A linearly displaceable actuator pin 212 is disposed at the opposite end of the bellows 211. Polar electrolyte 215 passes from chamber 208 to chamber 209 via the porous dielectric 210 upon the application of an electric field or potential to spaced-electrodes or electrode-arrays 220. The porous dielectric 210 may include non-porous particles, high surface area structures fabricated within the channel, or microporous such as monolithic polymer networks. Porous dielectric 210 offers at a minimum significant resistance or may prevent the polar electrolyte 215 from moving from one chamber to the other naturally in the absence of an electric field or potential. Preferably, the electrokinetic actuator is biased to apply a minimum pressure or force even in the start position depicted in FIG. 2b. As shown in FIG. 2c, when an electric field or potential is applied across the electrodes 220, the polar electrolyte 215 is driven from chamber 208 to 209 due to electro-osmotic flow. This movement of polar electrolyte 215 expands the bellows 211 attached to chamber 209 with a pressure corresponding to Darcy permeability of the porous dielectric 210 and also the volume of the chamber 209 and the attached bellows 211. The displacement of the bellows 211 and the actuator pin 212 with the associated pressure supporting it is utilized as the actuation mechanism for controlling the valve mechanism 135 that controls fluid flow in a shunt. Pump performance in terms of pressure generated per volt of applied electric potential is determined by any one or more of several factors including composition of the porous dielectric material, the composition of the stationary phase and geometry as well as the properties of the electrolyte.

The electrokinetic actuator 200 includes a mechanical valve actuation mechanism to titrate or adjust the pressure at which the fluid pathway will open or even the size of the fluidic pathway itself. In FIGS. 2b and 2c, the mechanical valve actuation mechanism is the bellows 211 and actuator pin 212. Several alternative more complex mechanical valve actuation mechanisms exhibiting rotation, translation or a combination thereof are shown in FIGS. 3a, 3b, 4a, 4b, 5a, 5b and 6, however, different mechanical valve actuation mechanisms are contemplated and within the intended scope of the present invention. A brief description of each of the mechanical valve actuation mechanisms is provided below.

FIGS. 3a & 3b shows a mechanical valve actuation mechanism including a rack-n-pinion gear in combination with a coil-spring and a linear extension or bias plate 241. Rack and pinion gear converts or translates rotation into linear motion or vice-versa. The relatively flat, toothed part is the rack 230 and the gear 235 is the pinion. Rack 230 and pinion gear 235 each have formed or cut therein complementary teeth which mesh or engage with one another. The speed with which the pinion gear turns as the rack advances or retreats is determined by the diameter of the pinion gear and geometric ratios of the teeth. Pinion gear 235, in turn, is connected to one end of a coil-spring 240 while the opposite end of the coil-spring 240 is connected to a proximal end of a bias plate 241. An opposite distal end of the bias plate 241 is affixed, fastened or secured to the valve mechanism 245 such as a ball-socket valve. Bias plate 241 is supported and held fixed by a guide/fulcrum 216.

In operation, an electric field is applied via a power source 170 to electrodes 220 producing an electro-osmotic force that moves electrolyte 215 from chamber 208 towards chamber 209 thereby expanding the bellows 211 and displacing the actuator pin 212 which, in turn, pushes, the proximal end of the rack 230 causing it to move to the right and rotate pinion gear 235 clock-wise, as depicted in FIG. 3a. Rotation of pinion gear 235, in turn, applies tension on the coil-spring 240 causing it to apply increased pressure via the bias plate 241 on the valve mechanism 245 thereby restricting fluid flow. This increase in pressure on the valve mechanism 245 will increase the resistance on the valve mechanism opening and thereby decreasing the rate of drainage. As a corollary, one may reverse the field applied via the power source 170 to the electrodes 220 accordingly producing an electro-osmotic force that moves electrolyte 215 towards chamber 208 thereby causing the bellows 211 to collapse and move the rack 230 to the left and unwind the coil-spring 240, as shown in FIG. 3b. This collapse or reverse movement will also be aided by the energy stored within the coil-spring 240. The release in energy from the coil-spring 240 will, in turn, reduce the pressure applied by the bias plate 241 on the valve mechanism 245 decreasing the resistance at the valve mechanism opening and thereby increasing the rate of drainage.

Figure 4A:
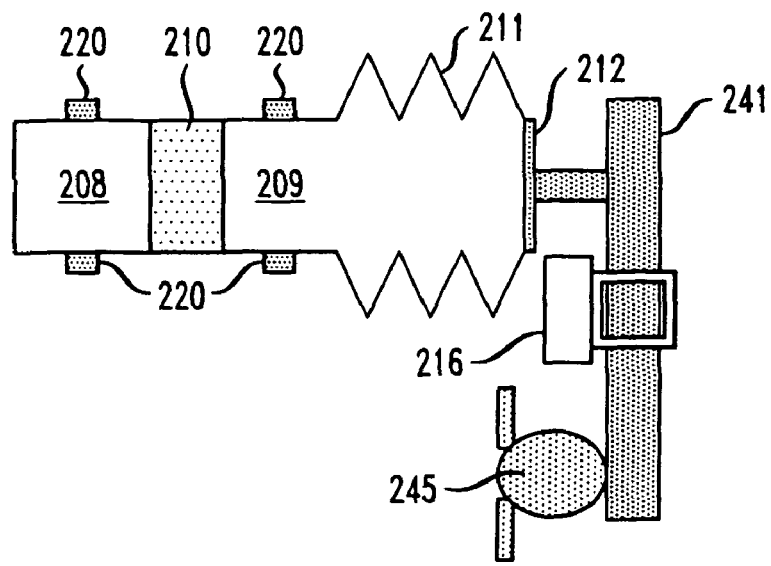
FIGS. 4a & b are schematic diagrams of a translational mechanical valve actuation mechanism for the electrokinetic actuator of FIG. 2a, wherein the mechanical valve actuation mechanism is a bias-spring, wherein an initial starting position in which the bias-spring is subject to minimum force from the actuator pin is depicted in FIG. 4a, while a final position subject to maximum force in the presence of an applied electric field is depicted in FIG. 4b.
Figure 4B:
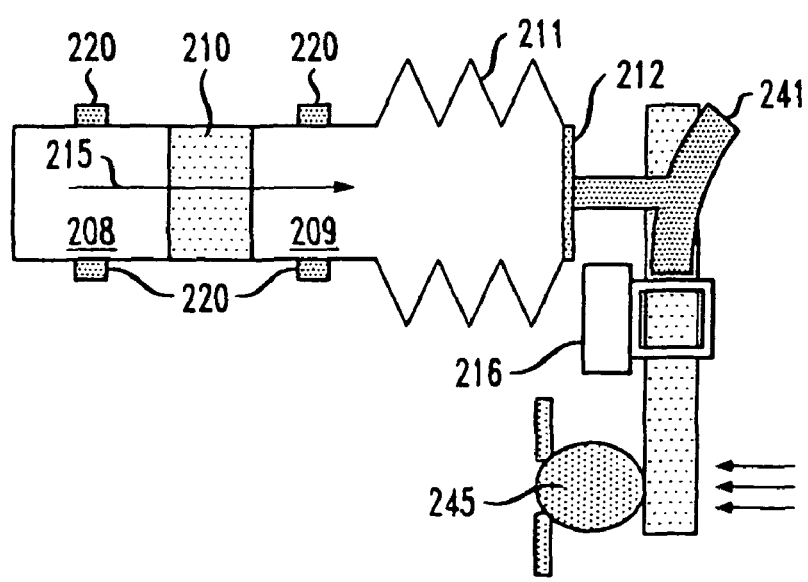

An alternative embodiment of a translational mechanical valve actuation mechanism is shown in FIGS. 4a & 4b wherein the bellows 211 is in contact with an actuator pin 212 which, in turn, is in contact with, a proximal end of a bias-plate 241 whereas its opposite distal end is affixed, fastened or secured to the valve mechanism 245 such as a ball-socket valve. In operation, an electric field is applied via a power source 170 to electrodes 220 producing an electro-osmotic force that moves electrolyte 215 from chamber 208 towards chamber 209 thereby expanding the bellows 211 which, in turn, displaces actuator pin 212 that pushes against a proximal end of a bias-spring 241 causing it to deflect, as depicted in FIG. 4b. A counterbalancing force will thereby be created on the opposite distal end of the bias-spring 241 that increases the pressure on the valve mechanism 245 correspondingly increasing the resistance to opening and thereby decreasing the rate of drainage. As a corollary, one may reverse the field applied via the power source 170 to the electrodes 220 accordingly producing an electro-osmotic force that moves electrolyte 215 from chamber 209 towards chamber 208 thereby causing the bellows 211 to collapse and displacing the actuator pin 212 to the left thereby releasing the tension on the proximal end of the bias-spring 241. This reverse movement will also be aided by the energy stored within the bias-spring 241. The release in energy from the bias-spring 241 will, in turn, reduce the pressure applied on the valve mechanism 245 thereby decreasing the resistance to opening of the valve mechanism 245 and increasing the rate of drainage.

Figure 5A:
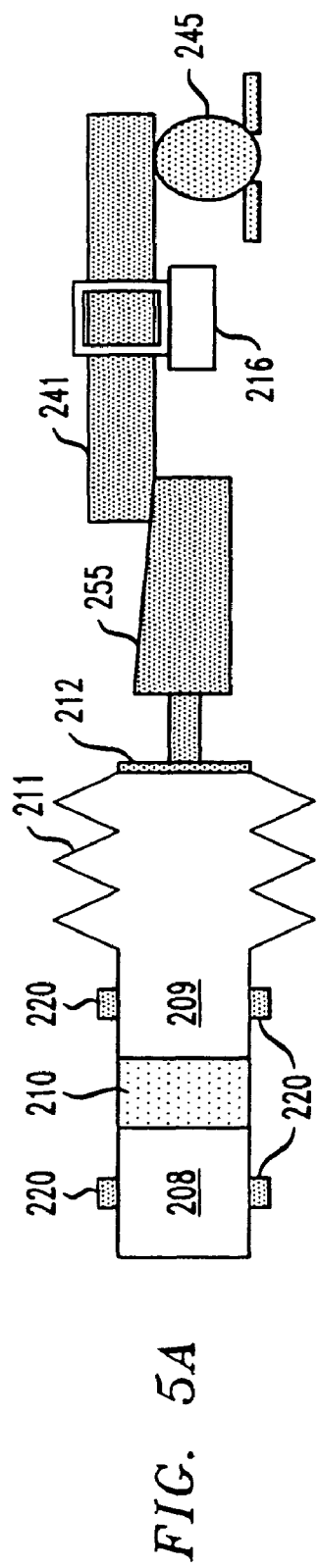
FIGS. 5a & b are schematic diagrams of a translational mechanical valve actuation mechanism for the electrokinetic actuator of FIG. 2a, wherein the mechanical valve actuation mechanism is a combination of a bias-spring and an increasing slope wedge member, wherein an initial start position in which the bias-spring is subject to minimum force from the wedge member is depicted in FIG. 5a, while a final position subject to maximum force in the presence of an applied electric field is depicted in FIG. 5b.
Figure 5B:
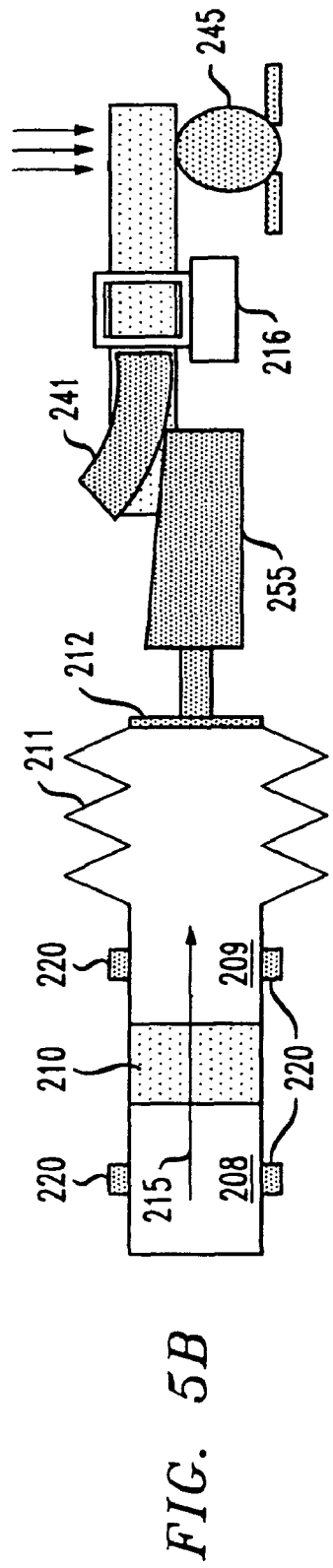

Still another embodiment of a translational mechanical valve driving mechanism is shown in FIGS. 5a & 5b, wherein one end of the bellows 211 is in contact with the actuator pin 212 while the opposite end of the actuator pin is in contact with an increasing slope wedge member 255 that moves under the bias-spring 241 affixed, fastened or secured to the valve mechanism 245 such as a ball-socket valve. In operation, an electric field is applied via a power source 170 to electrodes 220 producing an electro-osmotic force that moves electrolyte 215 from chamber 208 towards chamber 209 thereby expanding the bellows 211 and displacing the actuator pin 212 and wedge 255 to the right, as shown in FIG. 5b. Since the wedge 255 has an increasing slope with its widest part at its proximal end that is connected to the actuator pin, displacement of the wedge 255 pushes the proximal end of the bias-spring 241 upward causing the energy contained within it to increase. This increase in energy will result in increased pressure on the valve mechanism 245 and thus increase the resistance to opening; thereby decreasing the rate of drainage. As a corollary, one may reverse the field applied via the power source 170 to the electrodes 220 accordingly producing an electro-osmotic force that moves electrolyte 215 from the chamber 209 towards chamber 208 thereby causing the bellows 211 to collapse and the wedge 255 to move to the left. This reverse movement will also be aided by the energy stored within the bias-spring 241 and, in turn, reduces the pressure applied by the bias-spring 241 on the valve mechanism 245; resulting in decreased resistance at the opening and thereby increasing the rate of drainage.

All embodiments of the mechanical valve actuator mechanism described above may not only finely titrate the fluid flow therethrough but are also adapted to permit full fluid flow or cease or close off completely all fluid flow.

Figure 6:
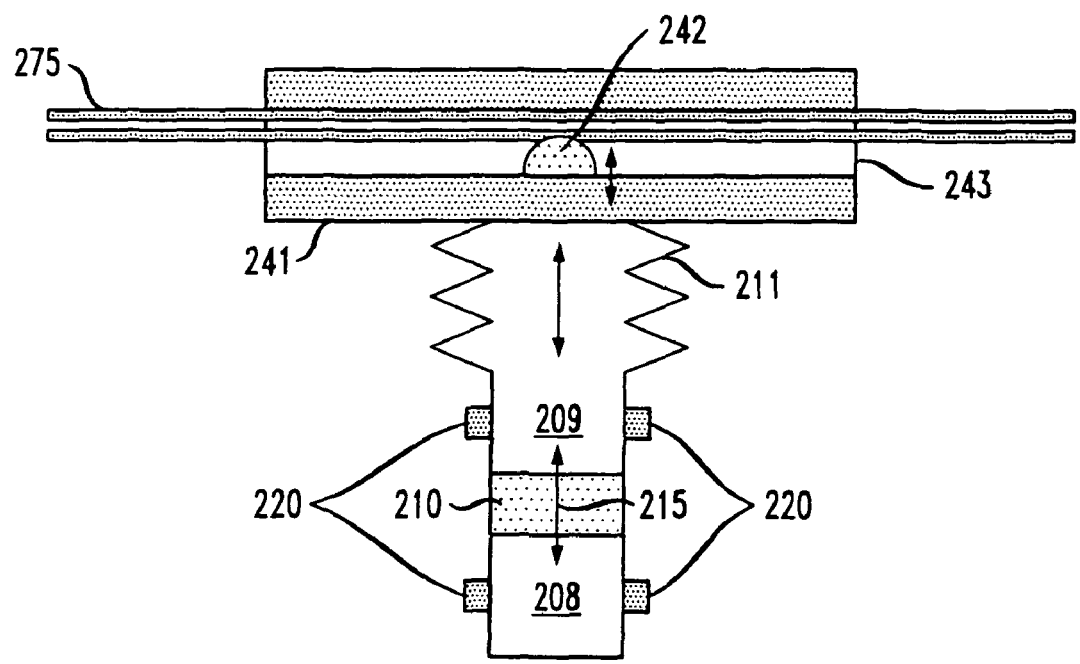
FIG. 6 is a schematic diagram of an electrokinetic actuator wherein the mechanical valve actuation mechanism is a constrictor block and hemispherical constrictor for compressing a flexible tubing through which fluid flows.

In this last embodiment represented in FIG. 6, the flexible tubing 275 in which drainage of the fluid therethrough is to be controlled or regulated is received within a channel 243 of a constrictor block 241. One side of constrictor block 241 is preferably connected directly to one end of the bellows 211 thereby eliminating the actuator pin 212 in order to maximize the surface area of contact. A constrictor 242, preferably hemispherical in shape, is disposed within the channel 243 between the flexible tubing 275 and the side of the constrictor block 241 connected to the bellows 211. The constrictor 242 and constrictor block 241 are preferably made from a magnetic resonance imaging (MRI) compatible thermoset polymer, glass, natural stone (e.g., ruby), hardened metal or alloy. Materials used for the constrictor 242 and constrictor block 241 may be the same or different. Constrictor 242 pushes against the flexible tubing 275 made of a biocompatible flexible and elastic material, for example, silicone or polyurethane. In operation, an electric field is applied via a power source 170 to electrodes 220 producing an electro-osmotic force that moves electrolyte 215 from chamber 208 towards chamber 209 thereby expanding the bellows 211 which, in turn, pushes the constrictor block 241 upward. The upward displacement of constrictor block 241 and constrictor 242 imposes a force against flexible tubing 275 causing it to deform and thereby restricting the cross-sectional size of the passage available for the fluid to drain therethrough. The preferred hemispherical shape of constrictor 242 distributes the pressure more gradually than a sharp edge and minimizes any damage to the flexible tubing with long-term operation. As a corollary, the electric field applied via the power source 170 to the electrodes 220 may be reversed producing an electro-osmotic force that moves electrolyte 215 from chamber 209 towards chamber 208 thereby causing the bellows 211 to collapse and reduce the pressure applied by the constrictor 242 on the flexible tubing 275 which will result in decreasing the resistance at the opening of valve member 245 and thereby increasing the rate of drainage. The embodiment depicted in FIG. 6 of the present invention is adapted to finely titrate or full fluid flow rather than close off fluid passage completely. Thus, the operation never closes off passage completely to prevent the passage of any fluid therethrough, but instead only titrates, adjusts or controls the size of the opening and rate of fluid flow by adjustment of the size, diameter or circumference of the channel 243. Flexible tube 275 is never restricted by the force imposed by constrictor 242 so as to completely close off and prevent passage of all fluid therethrough.

As previously mentioned, the present inventive electrokinetic actuator is not limited to only those mechanical value actuation mechanisms expressly disclosed and illustrated herein. Furthermore, the present inventive electrokinetic actuator to finely titrate fluid flow has been described with respect to a particular application of use with an externally programmable implantable shunt system for draining CSF. Other medical uses both implanted and external to the body as well as non-medical applications are contemplated and within the intended scope of the present invention.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An electrokinetic actuator for fluid flow titration comprising:
 a first chamber having a closed proximal end and an opposite open distal end;
 a second chamber having an open proximal end and an opposite open distal end, the open distal end of the first chamber being separated from the open proximal end of the second chamber by a porous dielectric disposed therebetween;
 a plurality of electrodes disposed about a perimeter of the first and second chambers; and
 polar electrolyte disposed within the actuator and adapted to pass through the porous dielectric between the first and second chambers upon the application of an electric field or electric potential to the plural electrodes; and
 a mechanical valve actuation mechanism connected to the open distal end of the second chamber for fine titration of a fluid using electro-osmosis of the polar electrolyte isolated to prohibit intermixing with the fluid being titrated;

wherein the mechanical valve actuation mechanism comprises:
a bellows having an open proximal end and an opposite distal end, the open proximal end of the bellows being connected to the open distal end of the second chamber;
an actuator pin having a proximal end connected so as to close off the open distal end of the bellows and an opposite distal end;
a rack connected to the distal end of the actuator pin, the rack having a plurality of teeth;
a pinion gear having complementary teeth and disposed so as to engage the teeth of the rack;
a coil-spring connected at a first end to the pinion gear and having an opposite second end;
a bias plate connected at a proximal end to the second end of the coil-spring and an opposite distal end, the bias plate being supported and held fixed by a fulcrum.

2. The electrokinetic actuator in accordance with claim 1, wherein the distal end of the bias plate is connected to a valve mechanism to adjust an opening thereof.

3. An implantable shunt system comprising:
a proximal catheter;
a drainage catheter;
a valve apparatus disposed between the proximal or drainage catheters; and
an electrokinetic actuator in accordance with claim 1 for finely titrating cerebrospinal fluid from the proximal catheter to the drainage catheter by controlling an opening pressure and/or diameter of the valve apparatus, wherein fine titration includes full fluid flow and/or complete cut off of fluid flow.

4. A drainage system comprising:
a proximal catheter;
a drainage catheter;
a valve apparatus disposed between the proximal or drainage catheters; and
an electrokinetic actuator in accordance with claim 1 for finely titrating fluid from the proximal catheter to the drainage catheter by controlling an opening pressure and/or diameter of the valve apparatus, wherein fine titration includes full fluid flow and/or complete cut off of fluid flow.

5. An electrokinetic actuator for fluid flow titration comprising:
a first chamber having a closed proximal end and an opposite open distal end;
a second chamber having an open proximal end and an opposite open distal end, the open distal end of the first chamber being separated from the open proximal end of the second chamber by a porous dielectric disposed therebetween;
a plurality of electrodes disposed about a perimeter of the first and second chambers;
polar electrolyte disposed within the actuator and adapted to pass through the porous dielectric between the first and second chambers upon the application of an electric field or electric potential to the plural electrodes; and
a mechanical valve actuation mechanism connected to the open distal end of the second chamber for fine titration of a fluid using electro-osmosis of the polar electrolyte isolated to prohibit intermixing with the fluid being titrated;
wherein the mechanical valve actuation mechanism comprises:
a bellows having an open proximal end and an opposite distal end, the open proximal end of the bellows being connected to the open distal end of the second chamber;
an actuator pin having a proximal end and an opposite distal end, the proximal end of the actuator pin connected so as to close off the distal end of the bellows;
a bias-spring connected at a proximal end to the distal end of the actuator pin and having an opposite distal end, the bias-spring being supported and held fixed by a fulcrum, the proximal end of the bias plate being deformable in response to the electrolyte passing from the first chamber to the second chamber upon the application of an electric field to the plural electrodes.

6. The electrokinetic actuator in accordance with claim 5, wherein the distal end of the bias plate is connected to a valve mechanism to adjust an opening thereof.

7. An electrokinetic actuator for fluid flow titration comprising:
a first chamber having a closed proximal end and an opposite open distal end;
a second chamber having an open proximal end and an opposite open distal end, the open distal end of the first chamber being separated from the open proximal end of the second chamber by a porous dielectric disposed therebetween;
a plurality of electrodes disposed about a perimeter of the first and second chambers;
polar electrolyte disposed within the actuator and adapted to pass through the porous dielectric between the first and second chambers upon the application of an electric field or electric potential to the plural electrodes; and
a mechanical valve actuation mechanism connected to the open distal end of the second chamber for fine titration of a fluid using electro-osmosis of the polar electrolyte isolated to prohibit intermixing with the fluid being titrated;
wherein the mechanical valve actuation mechanism comprises:
a bellows having an open proximal end and an opposite distal end, the open proximal end of the bellows being connected to the open distal end of the second chamber;
an actuator pin having a proximal end and a distal end, the proximal end of the actuator pin connected so as to close off the distal end of the bellows;
an increasing slope wedge member having a smaller distal end and an opposite larger proximal end connected to the distal end of the actuator pin;
a bias-spring having a proximal end supported by the distal end of the wedge member and an opposite distal end, the bias plate being supported and held fixed by a fulcrum.

8. The electrokinetic actuator in accordance with claim 7, wherein the distal end of the bias-spring is connected to a valve mechanism to adjust an opening thereof.

9. An electrokinetic actuator for fluid flow titration comprising:
a first chamber having a closed proximal end and an opposite open distal end;
a second chamber having an open proximal end and an opposite open distal end, the open distal end of the first chamber being separated from the open proximal end of the second chamber by a porous dielectric disposed therebetween;
a plurality of electrodes disposed about a perimeter of the first and second chambers;
polar electrolyte disposed within the actuator and adapted to pass through the porous dielectric between the first and second chambers upon the application of an electric field or electric potential to the plural electrodes; and
a mechanical valve actuation mechanism connected to the open distal end of the second chamber for fine titration of a fluid using electro-osmosis of the polar electrolyte isolated to prohibit intermixing with the fluid being titrated;
wherein the mechanical valve actuation mechanism comprises:
  a bellows having an open proximal end and an opposite open distal end, the open proximal end of the bellows being connected to the open distal end of the second chamber;
  a constrictor block having a channel defined longitudinally therethrough for receiving a flexible and elastic tubing, the open distal end of the bellows is connected to a perimeter of the constrictor block,
  a constrictor disposed in the channel between the tubing and the constrictor block connected to the bellows.

10. The electrokinetic actuator in accordance with claim 9, wherein the mechanical actuation mechanism does not allow complete cut off of fluid flow.

11. A method for fine titration of a fluid flow using an electrokinetic actuator for fluid flow titration comprising: a first chamber having a closed proximal end and an opposite open distal end; a second chamber having an open proximal end and an opposite open distal end, the open distal end of the first chamber being separated from the open proximal end of the second chamber by a porous dielectric disposed therebetween; a plurality of electrodes disposed about a perimeter of the first and second chambers; polar electrolyte disposed within the actuator and adapted to pass through the porous dielectric between the first and second chambers upon the application of an electric field or electric potential to the plural electrodes; and a mechanical valve actuation mechanism connected to the open distal end of the second chamber for fine titration of a fluid using electro-osmosis of the polar electrolyte isolated to prohibit intermixing with the fluid being titrated, comprising the steps of:
  imposing a mechanical force via the mechanical valve actuation mechanism on an opening of a valve member to adjust fluid flow therethrough;
wherein the imposing step comprises the steps of:
  applying an electric potential or electric field to the plural electrodes to produce electro-osmosis that displaces the electrolyte between the two chambers through the porous dielectric;
  expanding/contracting a bellows connected to the second chamber as a result of the electro-osmosis of the electrolyte;
  linearly displacing an actuator pin connected to the bellows as a result of the expansion/contraction of the bellows;
  adjusting a force imposed on the opening of the valve member based on the linear displacement of the actuator pin;
wherein the adjusting the force step comprises the steps of:
  linearly displacing a rack connected to the actuator pin, wherein the rack has a plurality of teeth;
  engaging the plural teeth of the rack in complementary teeth of a pinion gear so as to rotate and control tensioning of a coil-spring;
  displacing upward/downward a bias plate supported and held fixed by a fulcrum and connected at one end to the coil-spring, an opposite end of the bias plate being connected to the opening of the valve member thereby finely titrating fluid flow therethrough;
  wherein rotation of the pinion gear in a clockwise direction increases tensioning in the coil-spring reducing the opening of the valve mechanism, and rotation of the pinion gear in a counter-clockwise direction decreases tensioning in the coil-spring increasing the opening of the valve mechanism.

12. A method for fine titration of a fluid flow using an electrokinetic actuator for fluid flow titration comprising: a first chamber having a closed proximal end and an opposite open distal end; a second chamber having an open proximal end and an opposite open distal end, the open distal end of the first chamber being separated from the open proximal end of the second chamber by a porous dielectric disposed therebetween; a plurality of electrodes disposed about a perimeter of the first and second chambers; polar electrolyte disposed within the actuator and adapted to pass through the porous dielectric between the first and second chambers upon the application of an electric field or electric potential to the plural electrodes; and a mechanical valve actuation mechanism connected to the open distal end of the second chamber for fine titration of a fluid using electro-osmosis of the polar electrolyte isolated to prohibit intermixing with the fluid being titrated comprising the steps of:
  imposing a mechanical force via the mechanical valve actuation mechanism on an opening of a valve member to adjust fluid flow therethrough;
wherein the imposing step comprises the steps of:
  applying an electric potential or electric field to the plural electrodes to produce electro-osmosis that displaces the electrolyte between the two chambers through the porous dielectric;
  expanding/contracting a bellows connected to the second chamber as a result of the electro-osmosis of the electrolyte;
  linearly displacing an actuator pin connected to the bellows as a result of the expansion/contraction of the bellows;
  adjusting a force imposed on the opening of the valve member based on the linear displacement of the actuator pin;
wherein the adjusting the force step comprises the steps of:
  deflecting upward/downward a proximal end of a bias-spring connected to the actuator pin, the bias-spring being supported and held fixed by a fulcrum and a distal end of the bias-spring being connected to the opening of the valve member thereby finely titrating fluid flow therethrough;
  wherein deflection of the proximal end of the bias-spring upward imposes a counterbalancing opposite force on the distal end of the bias-spring that reduces the opening of the valve mechanism decreasing fluid flow therethrough, and reduced deflection of the proximal end of the bias-spring reduces the counterbalancing opposite force on the distal end of the bias-spring so as to increase the opening of the valve mechanism increasing fluid flow therethrough.

13. A method for fine titration of a fluid flow using an electrokinetic actuator for fluid flow titration comprising: a first chamber having a closed proximal end and an opposite open distal end; a second chamber having an open proximal end and an opposite open distal end, the open distal end of the first chamber being separated from the open proximal end of the second chamber by a porous dielectric disposed therebetween; a plurality of electrodes disposed about a perimeter of the first and second chambers; polar electrolyte disposed within the actuator and adapted to pass through the porous dielectric between the first and second chambers upon the application of an electric field or electric potential to the plural electrodes; and a mechanical valve actuation mechanism connected to the open distal end of the second chamber for fine titration of a fluid using electro-osmosis of the polar electrolyte isolated to prohibit intermixing with the fluid being titrated, comprising the steps of:

imposing a mechanical force via the mechanical valve actuation mechanism on an opening of a valve member to adjust fluid flow therethrough;

wherein the imposing step comprises the steps of:

applying an electric potential or electric field to the plural electrodes to produce electro-osmosis that displaces the electrolyte between the two chambers through the porous dielectric;

expanding/contracting a bellows connected to the second chamber as a result of the electro-osmosis of the electrolyte;

linearly displacing an actuator pin connected to the bellows as a result of the expansion/contraction of the bellows;

adjusting a force imposed on the opening of the valve member based on the linear displacement of the actuator pin;

wherein the adjusting step comprises the steps of:

linearly displacing a wedge member having an increasing slope with a maximum width at its proximal end which is connected to the actuator pin and a minimum width at its distal end;

deflecting upward/downward a proximal end of a bias-spring supported by the distal end of the wedge member, the bias-spring being supported and held fixed by a fulcrum and a distal end of the bias-spring being connected to the opening of the valve member thereby adjusting fluid flow therethrough;

wherein deflection of the proximal end of the bias-spring upward imposes a counterbalancing opposite force on the distal end of the bias-spring that reduces the opening of the valve mechanism decreasing fluid flow therethrough, and reduced deflection of the proximal end of the bias-spring reduces the counterbalancing opposite force on the distal end of the bias-spring so as to increase the opening of the valve mechanism increasing fluid flow therethrough.

14. A method for fine titration of a fluid flow using an electrokinetic actuator far fluid flow titration comprising: a first chamber having a closed proximal end and an opposite open distal end; a second chamber having an open proximal end and an opposite open distal end, the open distal end of the first chamber being separated from the open proximal end of the second chamber by a porous dielectric disposed therebetween; a plurality of electrodes disposed about a perimeter of the first and second chambers; polar electrolyte disposed within the actuator and adapted to pass through the porous dielectric between the first and second chambers upon the application of an electric field or electric potential to the plural electrodes; and a mechanical valve actuation mechanism connected to the open distal end of the second chamber for fine titration of a fluid using electro-osmosis of the polar electrolyte isolated to prohibit intermixing with the fluid being titrated, comprising the steps of:

imposing a mechanical force via the mechanical valve actuation mechanism on an opening of a valve member to adjust fluid flow therethrough;

wherein the imposing step comprises the steps of:

applying an electric potential or electric field to the plural electrodes to produce electro-osmosis that displaces the electrolyte between the two chambers through the porous dielectric;

expanding/contracting a bellows connected to the second chamber as a result of the displacement of the electrolyte;

adjusting a force imposed on a flexible tubing through which fluid flows therethrough thereby deforming a cross-sectional area of the flexible tubing;

wherein the adjusting the force step comprises the steps of:

imposing a force on a constrictor block disposed about a perimeter of the flexible tubing, the constrictor block having a longitudinal channel defined therethrough;

forcing into the flexible tubing a constrictor so as to alter the cross-sectional area of the flexible tubing, the constrictor being disposed in the channel between the flexible tubing and a portion of the constrictor block proximate the bellows.

15. The method in accordance with claim 14, wherein the constrictor is hemispherical in shape.

* * * * *